US012715831B2

(12) United States Patent
Watanabe et al.

(10) Patent No.: US 12,715,831 B2
(45) Date of Patent: Aug. 25, 2026

(54) METHOD FOR PRODUCING FLUORENONE

(71) Applicant: MITSUBISHI GAS CHEMICAL COMPANY, INC., Chiyoda-ku (JP)

(72) Inventors: Yuki Watanabe, Okayama (JP); Hiroki Sumi, Okayama (JP); Hideaki Fujita, Okayama (JP); Goh Nakamura, Okayama (JP); Tatsuyuki Kumano, Okayama (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 639 days.

(21) Appl. No.: 18/251,771

(22) PCT Filed: Nov. 4, 2021

(86) PCT No.: PCT/JP2021/040545

§ 371 (c)(1),
(2) Date: May 4, 2023

(87) PCT Pub. No.: WO2022/102502

PCT Pub. Date: May 19, 2022

(65) Prior Publication Data

US 2023/0406800 A1 Dec. 21, 2023

(30) Foreign Application Priority Data

Nov. 13, 2020 (JP) ................................ 2020-189608

(51) Int. Cl.
*C07C 45/36* (2006.01)
*B01J 31/04* (2006.01)
*B01J 35/27* (2024.01)

(52) U.S. Cl.
CPC ............... *C07C 45/36* (2013.01); *B01J 31/04* (2013.01); *B01J 35/27* (2024.01)

(58) Field of Classification Search
CPC ............ C07C 45/36; B01J 35/27; B01J 31/04
See application file for complete search history.

(56) References Cited

U.S. PATENT DOCUMENTS

| | | | |
|---|---|---|---|
| 3,038,940 | A | 6/1962 | Serres, Jr. |
| 3,875,237 | A | 4/1975 | Niznik |
| 5,902,907 | A | 5/1999 | Takahashi et al. |
| 6,403,521 | B1 | 6/2002 | Ishii et al. |

FOREIGN PATENT DOCUMENTS

| | | | |
|---|---|---|---|
| CN | 1156715 | A | 8/1997 |
| DE | 1 940 051 | | 2/1971 |
| EP | 0 779 264 | A1 | 6/1997 |
| JP | 9-221 447 | A | 8/1997 |
| JP | 2001-70798 | A | 3/2001 |
| JP | 2001-247505 | A | 9/2001 |
| JP | 2007-182399 | A | 7/2007 |
| WO | WO-2015/131435 | A1 | 9/2015 |

OTHER PUBLICATIONS

International Search Report issued Dec. 28, 2021 in PCT/JP2021/040545 filed Nov. 4, 2021, 2 pages.

Toshifumi Dohi, et al., "Clean and Efficient Benzylic C—H Oxidation in Water Using a Hypervalent Iodine Reagent: Activation of Polymeric Iodosobenzene with KBr in the Presence of Montmorillonite-K10," Journal of Organic Chemistry, vol. 73, No. 18, 2008, pp. 7365-7368.

*Primary Examiner* — Amy C Bonaparte
*Assistant Examiner* — Derek Rhoades
(74) *Attorney, Agent, or Firm* — Oblon, McClelland, Maier & Neustadt, L.L.P.

(57) ABSTRACT

A method for producing fluorenone including a pretreatment step of heating fluorene in the presence of a lower aliphatic carboxylic acid, a bromine compound, and a metal catalyst, and an oxidation step of continuously supplying fluorene and oxygen to perform an oxidation reaction, in the order indicated.

20 Claims, No Drawings

METHOD FOR PRODUCING FLUORENONE

CROSS-REFERENCE TO RELATED APPLICATIONS

The present application is a 35 U.S.C. § 371 National Stage Application of International Patent Application PCT/JP2021/040545, filed Nov. 4, 2021, which is based on and claims the benefit of priority to Japanese Application No. 2020-189608, filed Nov. 13, 2020. The entire contents of these applications are incorporated herein by reference.

TECHNICAL FIELD

The present invention relates to a method for producing fluorenone.

BACKGROUND ART

Fluorenone is used as a starting material or intermediate for chemicals, resins, etc. Specifically, fluorenone is a very useful compound as a starting material for electrophotographic photoreceptors, a starting material for colors, and a starting material for optical resins.

As a method for producing fluorenone, a method of oxidizing fluorene is performed. In particular, a production method by liquid phase oxidation using an oxygen-containing gas such as air has been developed.

For example, in PTL1, for the purpose of producing fluorenones at a high yield, a method for producing fluorenones including oxidizing fluorenes with molecular oxygen in an organic solvent in the presence of a phase transfer catalyst and a solid alkali metal hydroxide is disclosed.

Further, in PTL2, for the purpose of producing fluorenone at a high yield, a method of reacting a dimethyl sulfoxide solution of fluorene with oxygen molecules in the presence of a small amount of alkali metal hydroxide is disclosed.

In PTL3, for the purpose of easily and economically producing diallyl ketone at a high yield, a method of reacting an aromatic compound with oxygen molecules to produce a diallyl ketone using a lower saturated aliphatic monocarboxylic acid as solvent and a heavy metal as oxidation catalyst is disclosed, and a method for producing fluorenone is disclosed as an example thereof.

CITATION LIST

Patent Literature

PTL1: JP 2007-182399 A
PTL2: U.S. Pat. No. 3,875,237 B
PTL3: U.S. Pat. No. 3,038,940 B

SUMMARY OF INVENTION

Technical Problem

According to PTL3, a synthesis example of fluorenone by the so-called Amoco method is disclosed. In particular, by using ammonium bromide as a part of cocatalyst, a target product is obtained at a yield of 76%. However, the reaction requires supplying oxygen in the presence of acetic acid as solvent and heating at 205° C., so that there exists danger of catching fire and explosion. In particular, the increase in oxygen content in the off-gas (exhaust gas) causes a safety problem in industrial production.

On the other hand, changes of conditions for oxidation reaction such as reduction in the supply of oxygen, lowering of the reaction temperature, or alteration of the catalyst in order to avoid such danger cause decrease in the conversion ratio and selectivity, so that the yield of fluorenone as target product decreases.

Accordingly, there has been a demand for a safe industrial method for obtaining fluorenone at a high yield.

Therefore, it is an object of the present invention to provide a safe industrial method for producing fluorenone capable of obtaining fluorenone at a high yield, excellent in conversion ratio and selectivity.

Solution to Problem

As a result of extensive study by the present inventors, it has been found that the problem can be solved by heating fluorenone as starting material under specific conditions and continuously supplying fluorene and oxygen to perform an oxidation reaction.

In other words, the present invention relates to the following items [1] to [9].

[1] A method for producing fluorenone comprising a pretreatment step of heating fluorene in the presence of a lower aliphatic carboxylic acid, a bromine compound, and a metal catalyst, and an oxidation step of continuously supplying fluorene and oxygen to perform an oxidation reaction, in the order indicated.

[2] The method for producing fluorenone according to item [1], wherein the molar ratio between oxygen and fluorene continuously supplied [oxygen/fluorene] in the oxidation reaction is 0.5 to 4.0.

[3] The method for producing fluorenone according to item [1] or [2], wherein the heating temperature in the pretreatment step is 160 to 250° C.

[4] The method for producing fluorenone according to any one of items [1] to [3], wherein the heating time period in the pretreatment step is 3 to 30 minutes.

[5] The method for producing fluorenone according to any one of items [1] to [4], wherein the reaction temperature in the oxidation reaction is 120 to 250° C.

[6] The method for producing fluorenone according to any one of items [1] to [5], wherein the reaction pressure in the oxidation reaction is 0.1 to 3.0 MPa.

[7] The method for producing fluorenone according to any one of items [1] to [6], wherein the metal catalyst is at least one selected from the group consisting of a cobalt catalyst, a manganese catalyst, a zirconium catalyst, a nickel catalyst and a cerium catalyst.

[8] The method for producing fluorenone according to any one of items [1] to [7], wherein the lower aliphatic carboxylic acid is acetic acid.

[9] The method for producing fluorenone according to any one of items [1] to [8], wherein oxygen is supplied by introducing air in the oxidation step.

Advantageous Effects of Invention

According to the present production method, a safe industrial method for producing fluorenone capable of obtaining fluorenone at a high yield, excellent in conversion ratio and selectivity is provided.

DESCRIPTION OF EMBODIMENTS

A method for producing fluorenone comprises a pretreatment step of heating fluorene in the presence of a lower aliphatic carboxylic acid, a bromine compound, and a metal catalyst, and an oxidation step of continuously supplying fluorene and oxygen to perform an oxidation reaction, in the order indicated.

The production method of the present invention is described in detail as follows.

[Pretreatment Step]

In the method for producing fluorenone of the present invention, first, a pretreatment step of heating fluorene in the presence of a lower aliphatic carboxylic acid, a bromine compound, and a metal catalyst is performed.

<Lower Aliphatic Carboxylic Acid>

The lower aliphatic carboxylic acid used in the present step is preferably an aliphatic carboxylic acid having 1 to 4 carbon atoms, more preferably an aliphatic carboxylic acid having 2 to 3 carbon atoms, and still more preferably an aliphatic carboxylic acid having 2 carbon atoms.

Specific examples of the lower aliphatic carboxylic acid include preferably at least one selected from the group consisting of formic acid, acetic acid, propionic acid and butyric acid, more preferably at least one selected from the group consisting of acetic acid and propionic acid, and still more preferably acetic acid. In the case of using acetic acid, water and acetic acid may be mixed to prepare a mixed solution in advance for use as described later, or only acetic acid may be used. From the viewpoint of more easily dissolving a bromine compound and a metal catalyst, an aqueous acetic acid as mixture of water and acetic acid is preferably used.

It is preferable to use the lower aliphatic carboxylic acid because the activity of the catalyst may be enhanced.

The amount of the lower aliphatic carboxylic acid used in the pretreatment step is preferably 10 to 1000 parts by mass, more preferably 50 to 400 parts by mass, still more preferably 70 to 200 parts by mass, and furthermore preferably 80 to 100 parts by mass relative to 100 parts by mass of the whole fluorene.

With an amount of the lower aliphatic carboxylic acid in the range, the viscosity may be made appropriate in the present pretreatment step and the subsequent oxidation step, so that easy handling is achieved. Further, control of the reaction heat is also achieved.

Incidentally, the term “the whole fluorene” means “the whole of fluorene introduced in a reaction container in a period from the present pretreatment step to the completion of the oxidation step for use in the oxidation reaction”. The same applies hereinafter.

One lower aliphatic carboxylic acid may be used alone, or two or more may be used in combination.

<Bromine Compound>

Examples of the bromine compound used in the present step preferably include hydrogen bromide, a bromide salt, and an organic bromine compound, more preferably include at least one selected from the group consisting of hydrogen bromide and a bromide salt, and still more preferably include hydrogen bromide.

Hydrogen bromide is preferably used as an aqueous solution.

Specific examples of the bromide salt include sodium bromide, potassium bromide, and ammonium bromide.

The amount of the bromine compound used in the pretreatment step in terms of bromine is preferably 0.01 to 5 parts by mass, more preferably 0.05 to 3 parts by mass, still more preferably 0.05 to 1 part by mass, and furthermore preferably 0.05 to 0.5 parts by mass, relative to 100 parts by mass of the whole fluorene.

It is preferable that the amount of the bromine compound be controlled in the range, because the reaction rate is improved in the present pretreatment step and the subsequent oxidation step and the yield is also improved while corrosion of the reaction container or the like is suppressed.

One bromine compound may be used alone, or two or more may be used in combination.

<Metal Catalyst>

The metal catalyst used in the present step is preferably at least one selected from the group consisting of a transition metal catalyst and a rare earth metal catalyst, more preferably a transition metal catalyst.

Preferably, examples of the specific transition metal catalyst include at least one selected from the group consisting of a cobalt catalyst, a manganese catalyst, a zirconium catalyst, a nickel catalyst, and a cerium catalyst, and more preferably, examples thereof include at least one selected from the group consisting of a cobalt catalyst and a manganese catalyst. Still more preferably, both of a cobalt catalyst and a manganese catalyst are used.

As described above, the specific metal catalyst used in the present step is preferably at least one selected from the group consisting of a cobalt catalyst, a manganese catalyst, a zirconium catalyst, a nickel catalyst, and a cerium catalyst, and more preferably at least one selected from the group consisting of a cobalt catalyst and a manganese catalyst. Still more preferably, both of a cobalt catalyst and a manganese catalyst are used.

A metal catalyst may be used in the form of a salt, an elemental metal, an oxide, a hydroxide, or the like. The metal catalyst used in the present step is preferably a salt, more preferably an aliphatic carboxylate, still more preferably a lower aliphatic carboxylate, and furthermore preferably an acetate. In particular, at least one selected from the group consisting of cobalt acetate and manganese acetate is furthermore preferred.

It is preferable to use the metal catalyst, because fluorenone can be obtained at a high yield.

The amount of the metal catalyst used in the pretreatment step in terms of metal elements is preferably 0.02 to 10 parts by mass, more preferably 0.05 to 5 parts by mass, still more preferably 0.1 to 3 parts by mass, and furthermore preferably 0.1 to 1 part by mass, relative to 100 parts by mass of the whole fluorene.

It is preferable that the amount of the metal catalyst be controlled in the range, because the reaction rates in the present pretreatment step and the subsequent oxidation step are improved and the yield is also improved while a side reaction is suppressed.

With a catalyst concentration equal to or more than the lower limit, the reaction rate is improved and the yield is also improved. With a catalyst concentration equal to or less than the upper limit, the catalyst cost is reduced and the reaction is not adversely affected.

One metal catalyst may be used alone, or two or more may be used in combination.

Although the reason why a production method including the present pretreatment step enables to obtain fluorenone at a high yield, excellent in conversion ratio and selectivity by a safe industrial method is not clear, the following may be presumed.

It is presumed that in the pretreatment step, heating fluorene in the presence of the catalyst allows a part of fluorene to make an active species, so that the oxidation reaction proceeds smoothly from the initial stage of introduction of oxygen. Accordingly, it is presumed that no accumulation of oxygen occurs, so that production with a high level of safety may be performed. Further, it is presumed that the starting materials are evenly consumed during reaction, so that a side reaction is suppressed and an excellent conversion ratio and selectivity are achieved with an improved yield.

<Water>

Water may be used in the present step. It is preferable to use water because a bromine compound is easily dissolved.

The amount of water used in the pretreatment step is preferably 1 to 200 parts by mass, more preferably 1 to 100 parts by mass, still more preferably 2 to 50 parts by mass, and furthermore preferably 3 to 10 parts by mass, relative to 100 parts by mass of the whole fluorene used as starting material in the oxidation reaction.

With a water content in the range, the bromine compound may be dissolved while preventing the catalytic activity from being lowered, so that the yield may be improved in the subsequent oxidation step.

<Conditions for Pretreatment Process, Etc.>

The amount of fluorene used in the present step is preferably 1 to 50 mass %, more preferably 2 to 40 mass %, still more preferably 3 to 30 mass %, and furthermore preferably 5 to 20 mass % relative to the whole fluorene used as starting material in the oxidation reaction.

It is preferable that the amount of fluorene used in the present step be controlled within the range, so that the increase in the molecular weight of fluorene due to a side reaction may be suppressed to prevent the resulting decrease in yield.

Further, the fluorene used in the present step may be introduced all at once and heated, or may be continuously and gradually introduced. The continuous introduction is preferred from the viewpoint of suppressing a side reaction.

The supplying rate in the continuous introduction is preferably 0.1 to 10 parts by mass/minute, more preferably 0.2 to 5 parts by mass/minute, and still more preferably 0.3 to 3 parts by mass/min, relative to 100 parts by mass of the whole fluorene.

The supplying rate of fluorene in the pretreatment step is preferably 4 to 1700 parts by mass/minute, more preferably 8 to 850 parts by mass/minute, still more preferably 13 to 400 parts by mass/minute, and furthermore preferably 130 to 300 parts by mass/minute, relative to 100 parts by mass of the metal catalyst.

The heating temperature in the pretreatment step is preferably 160 to 250° C., more preferably 180 to 250° C., still more preferably 200 to 250° C., furthermore preferably 220 to 250° C., and furthermore preferably 220 to 240° C.

It is preferable to set the heating temperature in the range because the reaction rate may be easily controlled.

The heating time period in the pretreatment step may be appropriately changed depending on the heating temperature, the amount of catalyst, starting materials, etc., the size of the reaction container, the method of introducing the starting materials, etc., being preferably 3 to 30 minutes, more preferably 3 to 20 minutes, still more preferably 3 to 15 minutes, and furthermore preferably 5 to 15 minutes.

It is preferable to set the heating time period within the range, because the polymerization of fluorene due to a side reaction and the accompanying decrease in yield are suppressed.

In the present step, from the viewpoint of safety, it is preferable to introduce an inert gas such as nitrogen into the reaction container containing the starting material before introducing oxygen. A trace amount of oxygen, which is present as an impurity in the inert gas and does not substantially contribute to the oxidation reaction, may be contained.

The present pretreatment step is a step which is performed before introducing oxygen. The starting point of the pretreatment step is when the heating temperature exceeds the minimum heating temperature of the set heating temperature (160° C. when heating is performed at 160 to 250° C.) for the first time in the presence of fluorene, a lower aliphatic carboxylic acid, a bromine compound and a metal catalyst. Incidentally, in the case where any of fluorene, the lower aliphatic carboxylic acid, the bromine compound and the metal catalyst is supplied after heating, the starting point of the present pretreatment step is when the heating temperature reaches the set heating temperature and all of fluorene, the lower aliphatic carboxylic acid, the bromine compound and the metal catalyst is present in a reaction container. For example, in the case where the heating temperature is controlled to a set heating temperature in the presence of a lower aliphatic carboxylic acid, a bromine compound and a metal catalyst, and then fluorene is supplied into a reaction container, the starting point of the pretreatment step is the time when fluorene is first supplied to the reaction container.

The end point of the present pretreatment step is when the heating temperature finally falls below the minimum temperature of the set heating temperature or when the supply of oxygen is started. Incidentally, in the case where the heating temperature falls below the minimum temperature of the set heating temperature during the present pretreatment step, the time period when the heating temperature falls below the minimum temperature of the set heating temperature is not included in the heating time period.

[Oxidation Step]

The method for producing fluorenone of the present invention includes the pretreatment step and a subsequent oxidation step of continuously supplying fluorene and oxygen to perform an oxidation reaction.

In the present oxidation step, in the presence of a lower aliphatic carboxylic acid, a metal catalyst and a bromine compound, residual fluorene other than fluorene added in the pretreatment step and oxygen are continuously supplied to oxidize fluorene, so that fluorenone is obtained.

Here, "continuously supplying fluorene and oxygen" means that the oxidation reaction of fluorene in a reaction container and the supply of fluorene and oxygen are performed in parallel, and fluorene and oxygen are supplied in a period exceeding 50% of the reaction time period from the start of the oxidation reaction to the end of the oxidation reaction.

In the method for producing fluorenone of the present invention, fluorenone as starting material is continuously supplied after the pretreatment step, so that fluorenone may be obtained at a high conversion ratio and a high selectivity under industrially safe conditions. Although the reason thereof is not clear, the following may be presumed.

A fluorene radical is generated by the pretreatment step. The subsequent continuous supply of fluorene and oxygen as starting materials allows the supplied oxygen to be sequentially used and consumed in the oxidation reaction from immediately after introduction, so that the oxygen content in the off-gas (exhaust gas) during reaction may be reduced. Accordingly, the reaction may be terminated in an industrially safe manner without reaching the explosion limit of the lower aliphatic carboxylic acid vapor. Furthermore, the reason why fluorenone is obtained at a high conversion ratio and a high selectivity is presumed as follows. The oxygen and the starting material supplied as described above are sequentially used in the oxidation reaction, so that the oxidation reaction proceeds without a side reaction caused by accumulation of the starting material in a reaction system.

<Oxidation Reaction Conditions, Etc.>

In the present step, fluorene and oxygen are continuously supplied.

Although the supplying rate of fluorene may be constant or may be appropriately changed during supply, it is preferable that the supplying rate be substantially constant in consideration of the convenience of supply.

The supplying rate of fluorene in the present oxidation step may be appropriately changed depending on the size of a reaction container, being preferably 0.1 to 10 parts by mass/min, more preferably 0.2 to 5 parts by mass/minute, and still more preferably 0.3 to 3 parts by mass/minute, relative to 100 parts by mass of the whole of fluorene.

The supplying rate of fluorene is preferably 4 to 1700 parts by mass/minute, more preferably 8 to 850 parts by mass, still more preferably 13 to 400 parts by mass/minute, and furthermore preferably 130 to 300 parts by mass/minute relative to 100 parts by mass of the metal catalyst, from the viewpoint of appropriately controlling the reaction and enhancing safety.

As the oxygen used in the present step, oxygen gas may be used, or a mixed gas with an inert gas or the like may be used. In particular, in the present step, it is preferable that oxygen be supplied by introducing air from the viewpoint of safety and economy.

Although the supplying rate of oxygen may be constant or may be appropriately changed during supply, it is preferable that the supplying rate be constant in consideration of the convenience of supply.

The supplying rate of oxygen may be appropriately changed depending on the size of the reaction container and the supplying rate of fluorene. The molar ratio between oxygen and fluorene continuously supplied in the present step [oxygen/fluorene] is preferably 0.5 to 4.0, more preferably 0.6 to 3.0, and still more preferably 0.7 to 2.5, furthermore preferably 0.8 to 2.0, and furthermore preferably 0.9 to 1.5.

It is preferable to set the supply ratio in the above range because the selectivity and yield of fluorenone are improved.

As described above, it is preferable that the supplying rates of fluorene and oxygen and the molar ratio between fluorene and oxygen to be supplied be substantially constant in terms of convenience as well as the improvement of safety and yield as the effects of the present invention. However, as the oxidation reaction proceeds, the ratio between starting material fluorene and oxygen remaining in the reaction system and the amount of fluorene radicals change, so that the oxygen content in the off-gas may change. In particular, in the case where the oxygen content in the off-gas increases, it is preferable to reduce the amount of oxygen supplied and the molar ratio between oxygen and fluorene to be supplied.

It is preferable to continuously supply oxygen even after completion of the supply of fluorene in order to complete the oxidation reaction. When the oxidation reaction is completed, oxygen is no longer absorbed and the oxygen content in the off-gas increases. The supply of oxygen is therefore terminated. From the viewpoint of safety, it is preferable to terminate the supply of oxygen when the oxygen content in the off-gas is less than the explosion limit of the lower aliphatic carboxylic acid.

The reaction temperature of the oxidation reaction is preferably 120 to 250° C., more preferably 140 to 250° C., still more preferably 200 to 250° C., furthermore preferably 220 to 250° C., and furthermore preferably 220 to 240° C.

It is preferable to set the reaction temperature in the above range because the conversion ratio is improved.

The reaction pressure of the oxidation reaction is preferably 0.1 to 3.0 MPa, more preferably 0.3 to 3.0 MPa, still more preferably 0.5 to 3.0 MPa, furthermore preferably 1.0 to 3.0 MPa, furthermore preferably 1.5 to 3.0 MPa, and furthermore preferably 1.5 to 2.5 MPa.

The reaction time period of the oxidation reaction may be appropriately changed depending on the reaction temperature, the amount of catalyst, starting materials, etc., the size of the reaction container, the supplying rate of starting materials, etc., being preferably 30 to 300 minutes, more preferably 60 to 200 minutes, and still more preferably 80 to 120 minutes.

In the present step, as described above, fluorene and oxygen are continuously supplied to the reaction mixture subjected to the pretreatment step, containing the lower aliphatic carboxylic acid, the metal catalyst and the bromine compound used in the pretreatment step, and a part of fluorene added in the pretreatment step.

As each component used in the present step, it is convenient and preferable to use the one used in the pretreatment step as it is.

Further, the lower aliphatic carboxylic acid, the metal catalyst and the bromine compound may be further added in the present step. The addition of the metal catalyst and the bromine compound enables the continuous reaction to continue for a long time period. In the case where these are added in the present step, it is preferable to supply them continuously like fluorene, and it is more preferable to supply them such that the amounts of the metal catalyst and fluorene supplied are within the above ranges.

[Other Steps]

The method for producing fluorenone of the present invention may have an optional step other than the pretreatment step and the oxidation step.

Examples of the optional step included in the method for producing fluorenone of the present invention include a solvent removal step and a distillation step.

The solvent removal step is a step of removing the lower aliphatic carboxylic acid and water, which are solvents having a boiling point lower than that of fluorenone as object of the present production method. By removing these solvents before removal of the by-products generated through the oxidation reaction and fluorene as starting material by a solvent removal step, the subsequent distillation step may be efficiently performed.

In the solvent removal step, in order to efficiently remove the solvent, the solvent may be removed by heat-distillation under reduced pressure, or the solvent may be heat-distilled under normal pressure.

The distillation step may be any method as long as the target fluorenone can be separated and recovered with high purity.

The distillation temperature may be appropriately adjusted to be about the boiling point of fluorenone under the pressure at the time of distillation (boiling point at 1 atm: 342° C.). For example, in the case where the distillation pressure is adjusted to 3 kPa, the distillation temperature is preferably 150 to 300° C., more preferably 160 to 250° C., still more preferably 180 to 240° C., and furthermore preferably 180 to 220° C.

In the case where a distillation column is used in the distillation step, low boiling point components are appropriately removed from the top of the column and high boiling point components are appropriately removed from the bottom of the column, so that high-purity fluorenone is collected.

EXAMPLES

The present invention will be specifically described based on Examples shown below, though the present invention is not limited thereto.

[Evaluation]

<Oxygen Content in Off-Gas>

The oxygen content in the off-gas was determined as follows.

Equipment: portable oxygen meter POT-101, manufactured by Shimadzu Corporation

Measurement method: The gas discharge pipe of an autoclave was connected to the oxygen meter, and the oxygen content in the off-gas was measured in real time and evaluated based on the following criteria.

Incidentally, it is preferable that the oxygen content in the off-gas is not higher than 8 vol %, which is the explosive limit of acetic acid as solvent, from the viewpoint of safety in industrial production. A lower oxygen content in the off-gas is preferred, because lower the content is, the higher the degree of freedom of reaction conditions is in terms of safety.

(Evaluation Criteria)

Good: During the oxidation reaction time period, the oxygen content in the off-gas was always 8 vol % or less.

Fair: During the oxidation reaction time period, the time period when the oxygen content in the off-gas exceeded 8 vol % was less than 10% of the oxidation reaction time period.

Poor: During the oxidation reaction time period, the time period when the oxygen content in the off-gas exceeded 8 vol % was 10% or more of the oxidation reaction time period.

<Conversion Ratio>

The amount (mol) of fluorene contained in the oxidation reaction product after the oxidation step was calculated by the internal reference method using gas chromatography (internal reference: triphenylmethane) and subtracted from the amount of fluorene (mol) in the starting material to determine the amount of fluorene consumed (mol).

The conversion ratio was determined from the amount of fluorene consumed and the amount of fluorene in the starting material based on the following formula. Incidentally, the conversion ratio is the conversion ratio of starting material.

$$\text{Conversion ratio (\%)(Amount of fluorene consumed (mol))/(Amount of fluorene in starting material (mol))} \times 100$$

The higher the conversion ratio is, the more efficiently the starting material can be converted to the product fluorenone, which is preferable.

<Fluorenone Selectivity/Fluorenone Yield>

The amount of fluorenone (mol) contained in the oxidation reaction product after the oxidation step (amount of fluorenone produced) was calculated based on the internal reference method using gas chromatography (internal reference: triphenylmethane).

The fluorenone selectivity was determined from the amount of fluorenone produced and the amount of fluorene in the starting material (the amount of fluorene consumed) based on the following formula.

$$\text{Selectivity (\%)=(Amount of fluorenone produced (mol))/(Amount of fluorene consumed (mol))} \times 100$$

Incidentally, the fluorenone yield is a value calculated as the product of the conversion rate and the fluorenone selectivity. The higher the fluorenone selectivity and the fluorenone yield are, the more efficiently the high-purity fluorenone is produced, which is preferable.

Example 1 (Production of Fluorenone)

(1. Pretreatment Step)

Cobalt acetate tetrahydrate, manganese acetate tetrahydrate, 48 mass % hydrogen bromide aqueous solution, glacial acetic acid, and water were mixed to obtain a catalyst solution having a cobalt metal atom concentration of 0.75 mass %, a manganese metal atom concentration of 0.75 mass %, a bromine ion concentration of 0.075 mass %, an acetic acid concentration of 88.425 mass %, and a water concentration of 10 mass %.

A titanium-made autoclave with an internal volume of 500 mL having a gas discharge pipe with a reflux condenser, a gas blow pipe, a continuous starting material feeding pump and a stirrer was charged with 150 g of the catalyst solution, and then the temperature was raised to 200° C. (set temperature: 190 to 210° C.), and the pressure was raised to 1.0 MPa. In 10 minutes, 14 g of fluorene was supplied. The throughput was 1.4 g/min.

(2. Oxidation Step)

After completion of the pretreatment step, the introduction of air was started at the same time as the start of supply of additional starting materials, and the starting materials and air were continuously supplied. In 97.1 minutes, 136 g of fluorene as starting material was supplied. The throughput was 1.4 g/min. Air was supplied at 1.90 L/min (oxygen equivalent: 0.40 L/min). After 1.8 hours from the start of air supply, the oxygen content in the off-gas reached 8 vol %, so that the supply was terminated. The oxidation reaction product was thus obtained. The resulting oxidation reaction product was extracted and analyzed as follows. The conversion ratio was 100%, the fluorenone selectivity was 84.1 mol %, and the fluorenone yield was 84.1 mol %. The results are shown in Table 1.

Example 2 (Production of Fluorenone)

An oxidation reaction product was obtained in the same manner as in Example 1, except that the supplying rate and supplying time period of air in “2. Oxidation step” were changed as shown in Table 1. The oxygen content in the off-gas and the evaluation results of the resulting product are shown in Table 1.

Example 3 (Production of Fluorenone)

In “1. Pretreatment step”, instead of the catalyst solution in Example 1, a catalyst solution prepared by mixing cobalt acetate tetrahydrate, manganese acetate tetrahydrate, 48 mass % hydrogen bromide aqueous solution, glacial acetic acid, and water to have an atomic content of cobalt metal of 0.24 mass %, an atomic content of manganese metal of 0.15 mass %, a bromine ion content of 0.18 mass %, an acetic acid content of 89.61 mass %, and a water content of 10 mass % was used, and the amount supplied, supplying rate, supplying time period of fluorene and temperature were changed as shown in Table 1. Incidentally, the set temperature was 220 to 240° C.

Furthermore, an oxidation reaction product was obtained in the same manner as in Example 1, except that the amount supplied, supplying rate, supplying time period of fluorene and temperature, the supplying rate and supplying time period of air and conditions (temperature and pressure) in "2. Oxidation step" were changed as shown in Table 1. The oxygen content in the off-gas and the evaluation results of the resulting product are shown in Table 1.

Example 4 (Production of Fluorenone)

An oxidation reaction product was obtained in the same manner as in Example 3, except that the supplying time period and supplying rate of fluorene and the supplying rate of air in "2. Oxidation step" were changed as shown in Table 1. The oxygen content in the off-gas and the evaluation results of the resulting product are shown in Table 1.

Example 5 (Production of Fluorenone)

An oxidation reaction product was obtained in the same manner as in Example 3, except that the temperature in "1. Pretreatment step" was changed as shown in Table 1 (set temperature: 160 to 180° C.), and the temperature in "2. Oxidation step" was changed as shown in Table 1 (set temperature: 160 to 180° C.). The oxygen content in the off-gas and the evaluation results of the resulting product are shown in Table 1.

Example 6 (Production of Fluorenone)

An oxidation reaction product was obtained in the same manner as in Example 3, except that the temperature in "1. Pretreatment step" was changed as shown in Table 1 (set temperature: 160 to 180° C.). The oxygen content in the off-gas and the evaluation results of the resulting product are shown in Table 1.

Comparative Example 1 (Production of Fluorenone)

A catalyst solution described in "1. Pretreatment step" in Example 1 was prepared, and a titanium-made autoclave with an internal volume of 500 mL having a gas discharge pipe with a reflux condenser, a gas blow pipe, a continuous starting material feeding pump and a stirrer was charged with 150 g of the catalyst solution. "1. Pretreatment step" was not performed.

(2. Oxidation Step)

At the same time as the start of supply of fluorene as starting material, the introduction of air was started, and the starting material and air were continuously supplied. In 48.4 minutes, 150 g of fluorene as starting material was supplied. The throughput was 3.1 g/min. Air was supplied at 2.50 L/min (oxygen equivalent: 0.52 L/min). Immediately after the start of air supply, the oxygen content in the off-gas exceeded 8 vol %, and until the end of air supply, and the oxygen content in the off-gas has exceeded 8 vol % (minimum content: 11 vol %, maximum content: 20 vol %). The oxidation reaction product was thus obtained. The oxygen content in the off-gas and the evaluation results of the resulting product are shown in Table 1.

Comparative Example 2 (Production of Fluorenone)

(1. Pretreatment Step)

The catalyst solution described in "1. Pretreatment step" in Example 1 was prepared, and a titanium-made autoclave with an internal volume of 500 mL having a gas discharge pipe with a reflux condenser, a gas blow pipe, a continuous starting material feeding pump and a stirrer was charged with 150 g of the catalyst solution, and then the temperature was raised to 200° C. (set temperature: 190 to 210° C.) and the pressure was raised to 1.0 MPa under nitrogen atmosphere. For 10 minutes, 150 g of fluorene was heated.

(2. Oxidation Step)

After completion of the pretreatment step, introduction of air was started to supply air only. The air was supplied at 1.90 L/min (oxygen equivalent: 0.40 L/min). After 2 hours from the start of the air supply, the supply was terminated. An oxidation reaction product was thus obtained. The oxygen content in the off-gas and the evaluation results of the resulting product are shown in Table 1.

TABLE 1

| | | | Example 1 | Example 2 | Example 3 | Example 4 |
|---|---|---|---|---|---|---|
| Pretreatment step | Fluorene | Amount supplied | 14 g | 14 g | 6.5 g | 6.5 g |
| | | Supplying time period | 10 minutes | 10 minutes | 5 minutes | 5 minutes |
| | | Supplying rate | 1.4 g/minutes | 1.4 g/minutes | 1.3 g/minutes | 1.3 g/minutes |
| | Condition | Temperature | 200° C. | 200° C. | 230° C. | 230° C. |
| Oxidation reaction step | Fluorene | Amount supplied | 136 g | 136 g | 143.5 g | 143.5 g |
| | | Supplying time period | 97.1 minutes | 97.1 minutes | 87 minutes | 50 minutes |
| | | Supplying rate | 1.4 g/minutes | 1.4 g/minutes | 1.7 g/minutes | 2.9 g/minutes |
| | Air (oxygen) | Supplying rate | 1.90 L/minutes | 1.40 L/minutes | 2.30 L/minutes | 2.10 L/minutes |
| | | Supplying rate (oxygen equivalent) | 0.40 L/minutes | 0.29 L/minutes | 0.50 L/minutes | 0.50 L/minutes |
| | | Supplying time period | 1.8 hours | 2.7 hours | 1.5 hours | 1.5 hours |
| | Molar ratio oxygen/fluorene supplied | | 1.3 | 1.0 | 1.4 | 1.1 |
| | Condition | Temperature | 200° C. | 200° C. | 230° C. | 230° C. |
| | | Pressure | 1.0 MPa | 1.0 MPa | 2.0 MPa | 2.0 MPa |
| Evaluation | Oxygen content in off-gas | | Good | Good | Good | Good |
| | Conversion ratio | [%] | 100 | 98.2 | 100 | 100 |
| | Fluorenone selectivity | [mol %] | 84.1 | 74.8 | 98.4 | 84.0 |
| | Fluorenone yield | [mol %] | 84.1 | 73.4 | 98.4 | 84.0 |

TABLE 1-continued

| | | | Example 5 | Example 6 | Comparative Example 1 | Comparative Example 2 |
|---|---|---|---|---|---|---|
| Pretreatment step | Fluorene | Amount supplied | 6.5 g | 6.5 g | — | 150 g |
| | | Supplying time period | 5 minutes | 5 minutes | — | 10 minutes |
| | | Supplying rate | 1.3 g/minutes | 1.3 g/minutes | — | — |
| | Condition | Temperature | 170° C. | 170° C. | — | 200° C. |
| Oxidation reaction step | Fluorene | Amount supplied | 143.5 g | 143.5 g | 150 g | — |
| | | Supplying time period | 87 minutes | 87 minutes | 48.4 minutes | — |
| | | Supplying rate | 1.7 g/minutes | 1.7 g/minutes | 3.1 g/minutes | — |
| | Air (oxygen) | Supplying rate | 2.30 L/minutes | 2.30 L/minutes | 2.50 L/minutes | 1.90 L/minutes |
| | | Supplying rate (oxygen equivalent) | 0.50 L/minutes | 0.50 L/minutes | 0.52 L/minutes | 0.40 L/minutes |
| | | Supplying time period | 1.5 hours | 1.5 hours | 2.5 hours | 2 hours |
| | Molar ratio oxygen/fluorene supplied | | 1.4 | 1.4 | 1.0 | — |
| | Condition | Temperature | 170° C. | 230° C. | 200° C. | 200° C. |
| | | Pressure | 2.0 MPa | 2.0 MPa | 1 MPa | 1 MPa |
| Evaluation | Oxygen content in off-gas | | Good | Good | Poor | Good |
| | Conversion ratio | [%] | 100 | 100 | 93.6 | 88.5 |
| | Fluorenone selectivity | [mol %] | 86.3 | 97.3 | 67.4 | 50.1 |
| | Fluorenone yield | [mol %] | 86.3 | 97.3 | 63.1 | 44.3 |

From the results of Examples shown in Table 1, it is shown that the production method of the present invention enables to obtain high purity fluorenone at a high yield, excellent in conversion ratio and selectivity. Further, it is also shown that the method is industrially highly safe because the oxidation reaction is performed while suppressing the oxygen content in the off-gas.

The invention claimed is:

1. A method for producing fluorenone, the method comprising, in the order indicated:

heating fluorene in the presence of a lower aliphatic carboxylic acid, a bromine compound, and a metal catalyst; and continuously supplying fluorene and oxygen to perform an oxidation reaction.

2. The method of claim 1, wherein a molar ratio of the oxygen with respect to the fluorene continuously supplied in the oxidation reaction is in a range of from 0.5 to 4.0.

3. The method of claim 1, wherein the heating is at a temperature in a range of from 160 to 250° C.

4. The method of claim 1, wherein the heating is for a time period in a range of from 3 to 30 minutes.

5. The method of claim 1, wherein a reaction temperature in the oxidation reaction is in a range of from 120 to 250° C.

6. The method of claim 1, wherein a reaction pressure in the oxidation reaction is in a range of from 0.1 to 3.0 MPa.

7. The method of claim 1, wherein the metal catalyst is at least one selected from the group consisting of a cobalt catalyst, a manganese catalyst, a zirconium catalyst, a nickel catalyst, and a cerium catalyst.

8. The method of claim 1, wherein the lower aliphatic carboxylic acid is acetic acid.

9. The method of claim 1, wherein oxygen is continuously supplied by introducing air.

10. The method of claim 2, wherein the heating is at a temperature in a range of from 160 to 250° C.

11. The method of claim 2, wherein the heating is for a time period in a range of from 3 to 30 minutes.

12. The method of claim 2, wherein oxygen is continuously supplied by introducing air.

13. The method of claim 3, wherein the heating is for a time period in a range of from 3 to 30 minutes.

14. The method of claim 3, wherein oxygen is continuously supplied by introducing air.

15. The method of claim 4, wherein oxygen is continuously supplied by introducing air.

16. The method of claim 10, wherein the heating is for a time period in a range of from 3 to 30 minutes.

17. The method of claim 10, wherein oxygen is continuously supplied by introducing air.

18. The method of claim 11, wherein oxygen is continuously supplied by introducing air.

19. The method of claim 13, wherein oxygen is continuously supplied by introducing air.

20. The method of claim 1, wherein an inert gas is introduced before introducing the oxygen.

* * * * *